United States Patent [19]

Aberson et al.

[11] 4,381,784
[45] May 3, 1983

[54] SANITARY APPLIANCE CONTAINING BLOOD GELLING AGENT

[75] Inventors: Gerard M. Aberson, Appleton, Wis.; Robin Powell-Toothman, Vancouver, Wash.

[73] Assignee: Kimberly-Clark Corporation, Neenah, Wis.

[21] Appl. No.: 234,673

[22] Filed: Feb. 17, 1981

[51] Int. Cl.³ ............................................. A61F 13/16
[52] U.S. Cl. ................................... 605/368; 128/156; 604/378
[58] Field of Search ........... 128/284, 285, 287, 290 R, 128/296, 156

[56] References Cited

U.S. PATENT DOCUMENTS

| | | | |
|---|---|---|---|
| 3,888,256 | 6/1975 | Studinger | 128/296 |
| 3,993,616 | 11/1976 | Gross | 128/296 |
| 4,090,013 | 5/1978 | Ganslaw et al. | 128/296 |
| 4,105,033 | 8/1978 | Chatterjee et al. | 128/285 |
| 4,179,416 | 12/1979 | Smith | 128/284 |
| 4,192,727 | 3/1980 | Ward | 128/284 |
| 4,232,674 | 11/1980 | Melican | 128/285 |

Primary Examiner—C. Fred Rosenbaum
Attorney, Agent, or Firm—Howard Olevsky; William D. Herrick

[57] ABSTRACT

An absorbent article for absorbing blood having a conventional absorbent includes a blood gelling agent to thicken and bind menstrual fluid within the absorbent.

9 Claims, 3 Drawing Figures

SANITARY APPLIANCE CONTAINING BLOOD GELLING AGENT

FIELD OF THE INVENTION

This invention relates to sanitary appliances and particularly those useful for absorbing blood containing fluids.

BACKGROUND OF THE INVENTION

Over the past several years, attempts have been made to design a sanitary napkin having improved adsorbent utilization and controlled staining and flow characteristics. Sanitary napkins are traditionally made from inexpensive cellulosic material. While these materials do provide absorbency when used without modification, they suffer from certain disadvantages. Menstrual fluid is not immobilized in wood pulp fluff or other conventional cellulosic absorbents. Because of this factor, when pressure is exerted which compresses these absorbents, the fluid is liberated and can either be pushed upward through a fluid permeable covering to contact the wearer or can run outward along the top surface of the absorbent and may promote side staining.

In an attempt to counteract these difficulties, fluid directional means have been used. These directional means which have been designed to move fluid rapidly through the top surface of absorbent material and/or directionally outward toward the ends of the napkin have tended to increase the absorptive efficiency and capacity of a napkin but, even with these improvements, saturated napkins still may liberate menstrual fluid.

Attempts have been made to at least partially immobilize menstrual fluid and increase the absorptive capacity of napkins by the inclusion of so-called superabsorbent material. This material is either modified cellulose or synthetic polymer with increased capability for absorbing aqueous solutions. The superabsorbent material is generally in the form of a cross-linked three dimensional structure which allows for the penetration of the aqueous component of menstrual fluid but the suspended plasma proteins and blood cells are too large to penetrate into this preformed superabsorbent material structure and are left as a partially hydrated and concentrated mass surrounding the particular superabsorbent material particle.

The interaction with superabsorbent material is further complicated in that the blood cells and plasma proteins present in menstrual fluid also appear to have a large affinity for the aqueous portion of the blood. This is thought to be the case because it has been heretofore impossible to dehydrate blood to such an extent that precipitation of the solids via the withdrawal of fluid by superabsorbent material occurs. Thus a balance in equilibrium is determined in any particular napkin by the relative magnitude of the affinities of the superabsorbent materials and the blood solids for the aqueous portion of the blood as well as the relative absolute amounts of each component.

While superabsorbent material traditionally absorbs the aqueous portion of blood containing fluids with extreme rapidity, initially the protein fraction of the blood surrounds the individual superabsorbent particles, because of this preferential absorption therefore the absorption of the fluid as a whole is decreased.

There have been a variety of other compounds and approaches utilized in an attempt to immobilize menstrual fluid and/or blood. One such approach is set forth in U.S. Pat. No. 3,669,103 which describes cross-linking superabsorbent materials of different chemical compositions. The result is a covalently cross-linked gel which can absorb aqueous fluid. The structure formed by this reaction is a three-dimensional polymeric chain network which is water-insoluble but, water-swellable. In blood, the swollen gel is surrounded by a viscous, partially dehydrated, blood solid residue.

Another attempt to immobilize blood or menstrual fluid is disclosed in U.S. Pat. No. 3,670,731 which teaches the utilization of cross-linked hydrocolloids such as hydrolyzed, cross-linked polyacrylamide or sulphonated polystyrene. Cross-linking agents are divinyl chlorides and these compounds are the typical covalently cross-linked three-dimensional network gels associated with typical superabsorbent systems.

Another example of this type of system is disclosed in U.S. Pat. No. 3,645,836 which discloses the preparation of "gel-forming fibers" by precipitating guar gum from water with isopropyl alcohol. This reaction would hardly form a true gel because it is difficult to see how the water-soluble guar gum molecules could become cross-linked except, perhaps, by mechanical entanglement. After absorbing aqueous fluid the fibrous material would most likely turn into a viscous solution rather than a true gel.

Yet another approach is that disclosed in U.S. Pat. No. 3,810,468 which describes a lightly cross-linked, water-insoluble superabsorbent material. Example 8 describes "various copolymers of mono-olefinic compounds with maleic anhydride which can be lightly cross-linked and reacted with ammonia or alkali to produce water-insoluble, highly water-swellable polymer products". Mono-olefinic compounds are ethylene, styrene or vinyl methyl ether. The patent further teaches that cross-linkages are introduced in the monomer charge or, "alternatively, the olefinicmaleic anhydride copolymer is prepared as a substantially linear polymer and then reacted with a cross-linking agent." In order to render the copolymer hydrophilic the material is placed in a pressure vessel and treated with ammonia gas to convert the maleic acid to the "half amide-half ammonium salt form".

U.S. Pat. Nos. 3,980,563 and 4,154,898 describe superabsorbent materials of differing chemical compositions including a maleic anhydride copolymer. All of these materials are slightly cross-linked, water-insoluble but water-absorbing compounds.

Another similar type of compound system is described in U.S. Pat. No. 3,983,095 which pertains to the preparation of water-insoluble water-swellable derivatives of a copolymer of maleic anhydride and at least one kind of suitable vinyl monomer in fiber form (fiber form exists when in the dry state). The fiber will form the same type of gel with aqueous fluid after it has been absorbed as those described above. Other patents of interest which form the same type of cross-linked three-dimensional gel structure involving water-insoluble materials are U.S. Pat. Nos. 4,192,727 and 4,051,086.

Another approach is that disclosed in U.S. Pat. No. 4,179,416 which relates to the formation of alloy fibers where a synthetic polymer is dispersed in a matrix of regenerated cellulose. The synthetic polymer is water-loving and non-crystalline. Because of these characteristics the fluid retention of the alloy fiber is larger than the pure regenerated cellulose fiber. One of the synthetic linear polymers mentioned is Gantrez AN-149 manufactured by GAF Corporation. Gantrez is a methyl vinyl ether/maleic anhydride copolymer. According to the procedure set forth in this procedure, Gantrez will become completely hydrolyzed after injection in the viscose dope and in the regeneration bath. In addition, the hydrolyzed Gantrez will be completely enveloped by the regenerated cellulose matrix and therefore, in this disclosure it could not react directly with blood or menstrual fluid.

With the exception of the last mentioned patent, all of the prior art approaches have been directed towards forming systems which are completed disordered covalent polymer networks. This system is described and categorized by J. P. Flory in an article in Far. Disc. Chem. Soc. 57; 7-18, 1974. In this article Flory develops a classification scheme built upon the structural criteria of the compounds used for forming various gelling agents. All of the prior art with the exception noted above, is categorized as a class 2 gel by the Flory classification.

Interestingly enough, U.S. Pat. No. 3,810,468 discussed previously discloses a lightly cross-linked polymer including an olefinic maleic anhydride for reaction with blood type fluids. It is thought that this is done to render the molecule more hydrophilic and as such, the compound no longer functions as an anhydride.

The general approach as set forth in the above patent disclosures involves the thickening or reaction of blood as if it were an aqueous fluid. Inevitably, all of the agents utilized to immobilize the blood samples are cross-linked to some extent and are at least partially insoluble in an aqueous environment due to this cross-linkage. All of the immobilizing agents with the possible exception noted, form class 2 gels due to the three-dimensional cross-linking discussed previously. None of the systems for thickening, however, contemplate the reaction with blood components itself to immobilize the solution. Such a system would allow for much more complete utilization of the material because it would complex with the entire solution of blood or menses rather than be part of the selective immobilization present with the class 2 gels which are part of the conventional approach.

SUMMARY OF THE INVENTION

According to this invention an absorbent device designed to absorb blood or blood-like fluids such as a sanitary napkin is combined with a blood gelling agent to increase the efficiency of the absorbent device by increasing the viscosity and/or immobilizing blood or blood-like material in the device resulting in an increase in fluid retention. This is accomplished by utilizing agents which form particulate disordered structures when combined with blood as set forth in the Flory gel classification. Blood gelling agents for purposes of this invention are, therefore, classified as agents which: react with the protein present in blood or menstrual fluid; which form particulate disordered structures according to the fourth class of gels defined by Flory; which are essentially completely water-soluble; essentially completely linear; i.e. non-cross-linked and which when placed in water will not form a class 4 gel without the presence of blood protein. The several features described in the preceding sentences clearly differentiate over the conventional approach to immobilizing blood and menstrual fluid discussed in the prior art. Surprisingly, several of the compounds and copolymers utilized as components of type 2 gelling systems can with proper treatment be employed as blood gelling agents in the subject invention. These blood gelling agents generally are of two types i.e. di-carboxylic anhydrides and polycations. In both instances, these classes of compounds form complexes dependent upon their reaction with free primary amino groups in available protein either from blood cells or from plasma present in menstrual fluid.

Suitable compounds which may be utilized as blood gelling agents include the maleic anhydride group of copolymers such as the Gantrez AN series of methyl vinyl ether/maleic anhydride copolymers. These compounds are sold in several different grades with the grades each representing a different range of molecular weights.

Another series of compounds which function according to the principles of this invention are the ethylene maleic anhydride resins made by Monsanto Industrial Chemicals Corporation, St. Louis, Missouri. Again, several grades are available in different molecular weight ranges.

In addition the styrene-maleic anhydride copolymers manufactured by Monsanto as Scripset resins are available for use according to the teachings of this invention. All of the compounds listed above are of the di-carboxylic anhydride type which, when partially hydrated and in solution with the caveats described below, react with the free amino groups in blood.

As mentioned above an alternative type of blood gelling agent is the large molecular weight cationic polyelectrolytes. This is so because plasma proteins tend to carry negative charges at the prevailing pH of blood and when these compounds are utilized a gel-like polyelectrolyte complex is formed. Examples of cationic agents according to this invention are WT 1700 and WT 1850 made by Calgon Corporation of Pittsburgh, Pennsylvania, which are acrylamide copolymers. Reten 210 is sold by Hercules Powder Company, Wilmington, Delaware, as a flocculation aid and is also an acrylamide copolymer. Another suitable polycation is Cellbond 120 an amphoteric guar gum made by Celanese Corporation of New York, New York.

There are several factors which affect the gelation of the di-carboxylic anhydride copolymers with blood. The gelation rate, inferred from the rate of viscosity increase, is rather slow. When a blood gelling agent is mixed or stirred into an aliquot of blood fluid, the maximum viscosity is reached after about one hour, depending on such variables as the agent concentration, pH and polymer dissolution rate. (The gelation rate should be even slower in a napkin where there is no mechanical stirring.)

This slow gelation rate is in contrast to the rate of blood fluid—superabsorbent interaction, which tends to be very rapid, initially. However, the initial gel material tends to block or impair continued fluid flow resulting in inefficient use of superabsorbents contained in a napkin (or other blood absorbing product).

It has been demonstrated that the blood gelling agent works effectively at the pH ranges associated with blood and menses i.e. between 6.2 and 7.2.

In the case of menstrual fluid, the addition of urine to menstrual fluid in a pad is not uncommon. It has been found that this addition weakens the intensity of the gel formation and is believed to function as a dilution factor.

One of the surprising features of the research done with both the ethylene maleic anhydride and Gantrez resins was that several of the samples did not form a gel with blood within six to eight hours while others formed a rigid gel within two hours. It has subsequently been determined that the samples which did not form gels within the extended period were "fresh" samples. The samples are sold as anhydrides and it has now been determined that it is necessary for at least part of the hydrophobic anhydrous di-carboxylic acid groups to be hydrated to form hydrophilic carboxyl groups for the gelling reaction to occur at all. These facts were confirmed by infrared spectroscopic analysis. It is theorized the reason for this is that the presence of carboxylic acid groups in the partially hydrated polymer increases solubility because the anhydrous Gantrez AN is extremely hydrophobic while the completely hydrated Gantrez S-97 which also does not form a gel with blood dissolves rapidly in water. Therefore, the presence of some hydrophilic carboxyl groups on a polymer chain segment with di-carboxylic anhydride groups appears to help solubilize the polymer molecules in aqueous blood fluid. This solubilized macromolecule, it is theorized, diffuses through the blood until the di-carboxylic anhydride groups react with primary amine groups of plasma protein to form a protein gel.

Another factor to be considered in the choice of a particular blood gelling agent is the molecular weight of the polymer. Among chemically identical samples, higher molecular weight polymers and copolymers produce more rigid gels and produce them more rapidly. The decision between higher molecular weight and lower molecular weight copolymers and polymers is generally a function of cost, however. This is so because the same effect can be obtained by increasing the concentration of a lower molecular weight polymer in the absorbent medium.

The other broad category of agents i.e. the polycationic gelling agents seem to react due to electrostatic forces in the same way to the variables set forth above: although, the precise mechanism of the interaction on each of the polycationic gelling agents with blood is not known at this time. What is known is that the polycationic gelling agents described react in the same manner when employed in similar concentrations in a sanitary napkin, albeit at a higher gelation rate.

Either type of blood gelling agent can be used at a level of 0.2 to 1.5 grams per sanitary napkin depending upon the variance discussed above as well as the location and purpose of the blood gelling agent. It is apparent, for example, that if the blood gelling agent is used in conjunction with conventional fluid direction means such as embossed lines or the like, the location of the blood gelling agent can be concentrated at or along the end of the embossed lines. Alternatively it may be desirable to blend the blood gelling agent uniformly with the absorbent component to provide an equal dispersion of the blood stain and increase the overall capacity of the napkin. A further alternative which is particularly preferred is to place the blood gelling agent in a uniform layer near the bottom of the napkin. The currently preferred configuration utilizes the conventional absorbent and then works to immobilize excess blood as the napkin becomes saturated. It is also possible to design a napkin of reduced thickness utilizing the blood gelling agent in conjunction with conventional cellulosic absorbents and relying upon the capillary suction of the cellulosic absorbent and subsequent immobilization by the gelling agent thereby allowing for reduction in bulk of the conventional absorbent component. A single intermediately positioned layer of blood gelling agent with or without suitable carriers or in conjunction with the superabsorbent materials are further embodiments also contemplated within the scope of the subject invention.

BRIEF DESCRIPTION OF THE DRAWINGS

The invention as related to sanitary napkins can be better understood by reference to the drawings in which.

Figure 1:
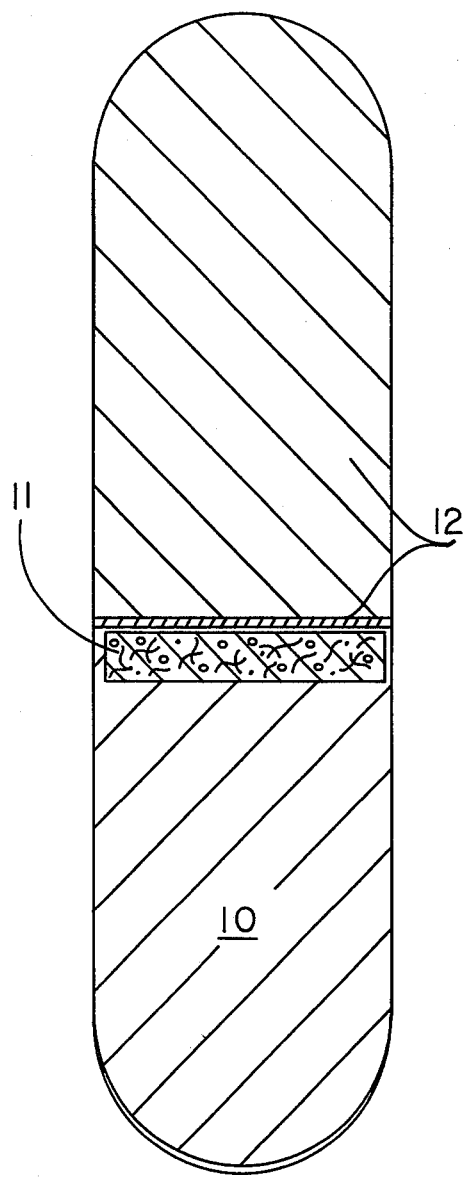
FIGS. 1 and 2 are plan views partially in cross section of alternative embodiments of the subject invention.

According to FIG. 1, a sanitary napkin having a fluid pervious cover 12 overlaying an absorbent layer containing blood gelling agents and conventional absorbents 11 rests on a fluid impervious baffle 10. The sanitary napkin thus illustrated shows a die cut configuration but configurations in which the fluid permeable cover material 12 encircle the baffle 10 are also contemplated and are for purposes of this invention substantially equivalent. Baffle configurations of different types in which the baffle extends along the sides of the absorbent batt and overlaps a portion of the top are well known in the art and are also contemplated within the scope of this invention with the benefits traditionally inherent in these various approaches acting in the same manner in the napkin according to the teachings set forth herein.

Figure 2:
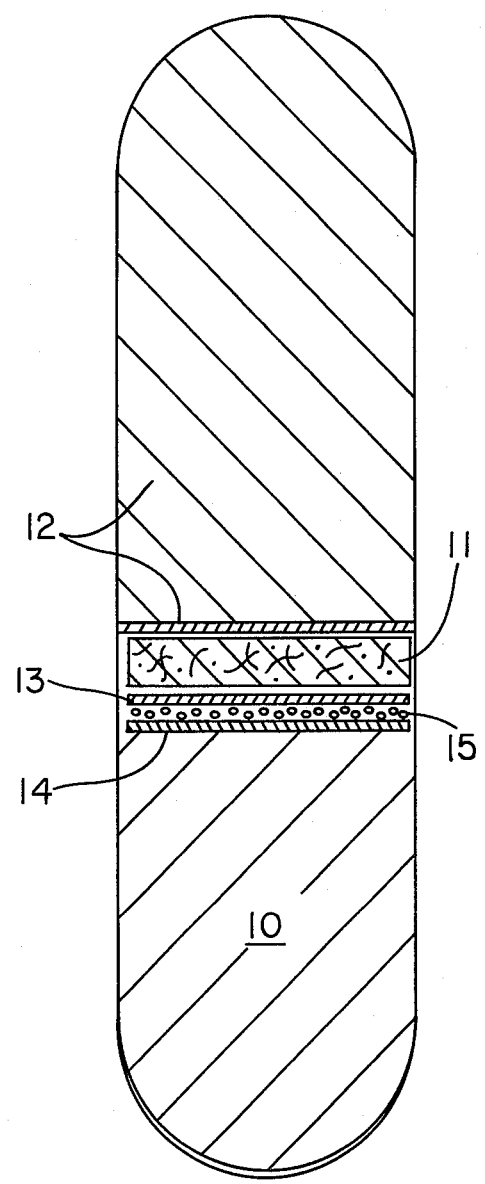

FIG. 2 is an alternative embodiment which is identical to FIG. 1 except that the blood gelling agent 15 rather than being present as an intermingled component dispersed homogeneously throughout the absorbent material is positioned between two layers of tissue which can be glued together with the aid of an atomized spray of water or a solution of dilute sodium carbonate depending upon the particular gelling agent. As mentioned above, the currently preferred method for positioning the blood gelling agent is against the baffle or at least on the bottom portion of the absorbent layer and this is one particularly preferred embodiment for accomplishing this goal. Of course it is possible to directly locate the gelling agent against the baffle and attach it to the baffle itself by conventional means such as print coating.

An example which more particularly illustrates the affect of the blood gelling agent on the absorbent properties of conventional wood pulp fluff is set forth below.

EXAMPLE

Two different gelling agents were tested in this example. Each was deposited in stripes 5/16" wide and ⅛" apart on one surface of a layer of conventional wood pulp fluff. The gelling agents were adhesively attached to the fluff surface using a spray of one percent sodium carbonate in water. The add on level based upon linear distribution was 4.3 grams per square foot. Samples were cut to produce a surface of 4×4 inches with ½ inch cut from each corner so that the entire sample surface area was 15.5 square inches. These samples and a control sample with no gelling agent were placed with the gelling side down in a horizontal position in a testing apparatus designed to place the sample under pressure to measure blood wicking.

Figure 3:
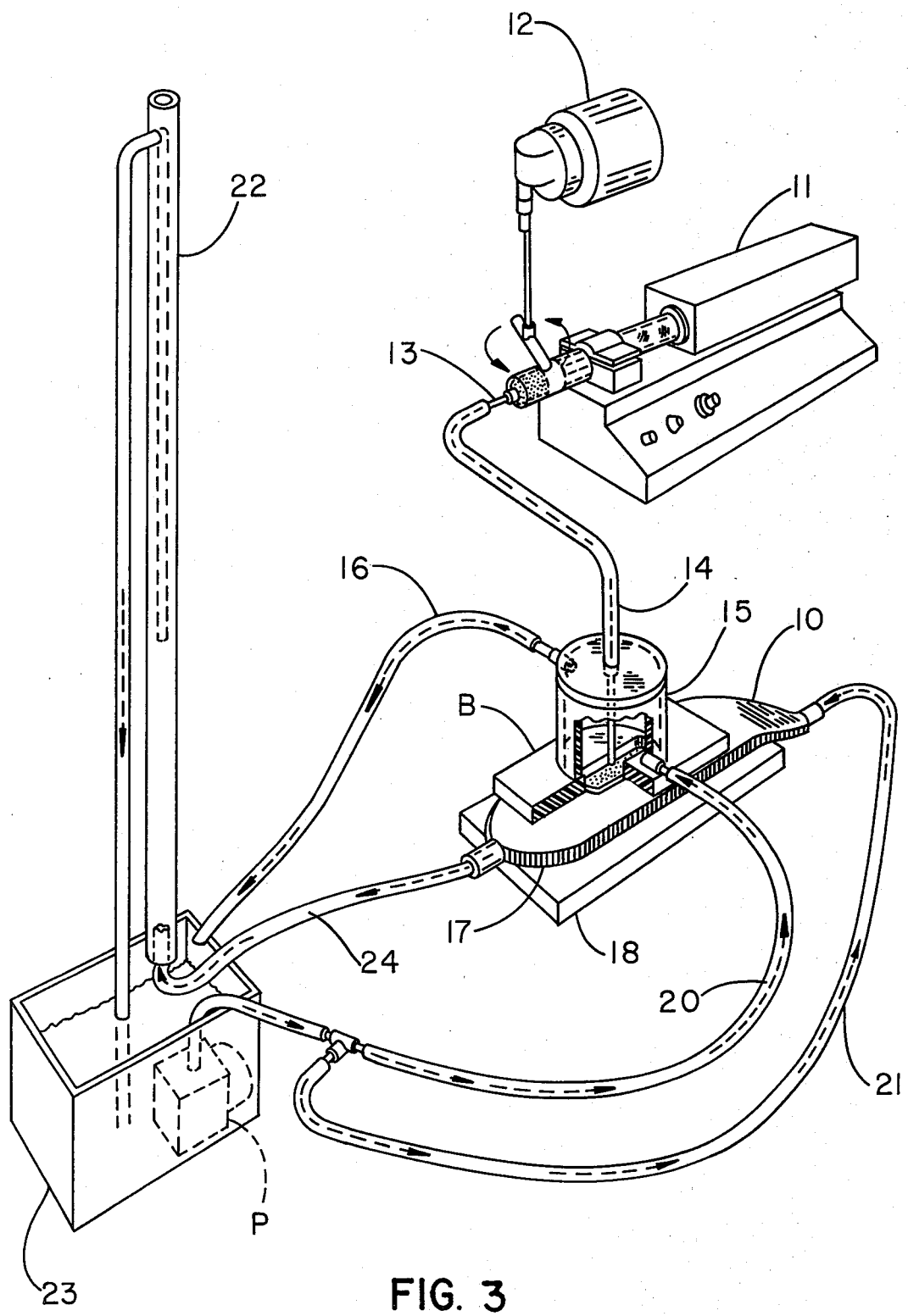

The testing apparatus as shown in FIG. 3 consists of a variable rate syringe pump and means for maintaining constant temperature and pressure on the sample. The fluid utilized for testing is bovine blood which has its hematocrit i.e. red blood cell level adjusted to a level of 20 percent of weight of the solution. The blood is fed by the pump 11 past a magnetic stirrer 12 through a syringe ejector 13 and into intake tube 14. Intake tube 14 leads into a hollow walled heat exchanger 15 which, as shown in partial cross section, rests upon a supporting block B which in turn rests upon the sample. A colostomy bag 10 is located beneath the samples and sits upon a support 18. The colostomy bag is fluidly connected with a constant temperature bath 23 through colostomy intake tube 21 via pump P. As shown in the drawings, pump P also provides the heat exchanger 15 with a temperature control water flow through water intake tube 20. Stand pipe 22 is also connected to the colostomy bag by pressure tube 24. The stand pipe in conjunction with the constant temperature bath 23 controls both temperature and pressure. The sample is maintained at a constant temperature of 37° C. which is body temperature by means of the constant temperature bath-generated fluid flow into the heat exchanger 15 through line tube 20 (with the fluid exiting from the heat exchanger jacket through exit conduit 16) and also through the flow through tube 21 into the colostomy bag 17.

The samples were placed under 1.7 pounds per square inch pressure and bovine blood with 30 percent hemotocrit was added to the samples from the top side at the center of the sample at a rate of three grams per hour for two hours at 37° C. (reflective of body temperature at the area of menstrual fluid discharge). After blood addition was discontinued, the sample was left in the wicking device for another hour to equilibrate and weighed to determine the exact amount of blood pickup. In addition the percent of top and bottom stain areas were determined.

Subsequently the samples were placed in a Buchner funnel and subjected to 5.5 inches of mercury suction pressure for three minutes to remove the free blood i.e. that in the sample which has not been retained by capillary tension. After the suction procedure, the sample is weighed again to determine the amount of blood that was retained. The results of these tests are set forth in the following table.

tion by the incorporation of the gelling agents of this invention and also controlled lateral movement of fluid is obtained by immobilizing the blood at the time of gellation.

It is apparent that with the concept of the subject invention the teachings can be used in a variety of methods. The blood gelling agents can be used in configurations of a variety of sanitary products not at all limited to sanitary napkins. It is only necessary that blood be a component of the body fluids to be absorbed.

What is claimed is:

1. An absorbent article used for absorbing body fluids containing blood including a fluid impervious baffle, an absorbent component and a blood gelling agent which is essentially non-cross-linked and water soluble and which forms particulate disordered structures with blood protein but not with water.

2. A sanitary napkin including a fluid impervious baffle, an absorbent component and a blood gelling agent which is essentially non-cross-linked and water soluble and which forms particulate disordered structures with blood protein but not with water.

3. The napkin according to claim 1 or 2 wherein the blood gelling agent is present at levels sufficient to at least partially immobilize the menstrual fluid.

4. The napkin according to claim 1 or 2 wherein the blood gelling agent is selected from a class consisting of medically safe partially hydrated di-carboxylic anhydride copolymer and polycations.

5. The napkin according to claim 1 or 2 wherein the blood gelling agent is present at a level of from 0.2 to 1.5 gm.

6. The napkin according to claim 2 wherein the blood gelling agent is present at a homogeneous blend with the absorbent.

7. The napkin according to claims 1 or 5 wherein the blood gelling agent is positioned near the baffle.

8. The napkin according to claims 1 or 2 wherein the blood gelling agent is present in a thin layer.

9. The napkin according to claim 1 or 2 wherein the blood gelling agent is used in combination with flow directing means.

TABLE I

| | | | | | After Vacuum Application | | | |
|---|---|---|---|---|---|---|---|---|
| Agent | Fluff gm. | Agent gm. | % Top Stain Area | % Bottom Stain Area | Gm. Blood Retained | Fluff Retaining Blood | Gm. Blood Retained By Agent | Gm. Blood Per Gm. Agent |
| Gantrez AN-169 | 5.91 | .46 | 28 | 23 | 4.24 | 1.51 | 1.84 | 17.4 |
| EMA 91 | 5.91 | .46 | 25 | 22 | 4.05 | 1.39 | 1.84 | 18.2 |
| Control (Woodpulp Fluff) | 5.49 | — | 35 | 38 | 3.18 | 2.00 | — | — |

Effect of Gelling Agents on Fluid Retention as Measured in the Laboratory

The results of these tests clearly indicate first, that there is a substantial increase in immobilized fluid reten-

* * * * *